(12) United States Patent
Abe

(10) Patent No.: US 8,603,355 B2
(45) Date of Patent: Dec. 10, 2013

(54) COMPOSITION FOR STABILIZING CHLORINE DIOXIDE

(75) Inventor: Koji Abe, Nishinomiya (JP)

(73) Assignee: Taiko Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/169,501

(22) Filed: Jun. 27, 2011

(65) Prior Publication Data

US 2011/0256244 A1 Oct. 20, 2011

Related U.S. Application Data

(62) Division of application No. 12/531,254, filed as application No. PCT/JP2008/052496 on Feb. 15, 2008, now abandoned.

(30) Foreign Application Priority Data

Mar. 15, 2007 (JP) ................................. 2007-067179

(51) Int. Cl.
 *C01B 11/02* (2006.01)
 *C01B 11/10* (2006.01)
 *A01N 59/08* (2006.01)

(52) U.S. Cl.
 USPC ..................................... 252/187.23; 424/661

(58) Field of Classification Search
 USPC .................................................. 252/187.23
 See application file for complete search history.

(56) References Cited

U.S. PATENT DOCUMENTS

| | | | |
|---|---|---|---|
| 2,988,514 A | 6/1961 | Robson et al. | |
| 4,044,103 A | 8/1977 | Molland et al. | |
| 4,104,190 A | 8/1978 | Hartshorn | |
| 4,880,556 A | 11/1989 | Hutchings | |
| 5,165,910 A | 11/1992 | Oikawa et al. | |
| 5,389,390 A | 2/1995 | Kross | |
| 6,200,557 B1 | 3/2001 | Ratcliff | |
| 6,231,830 B1 | 5/2001 | Madray | |
| 6,238,643 B1 | 5/2001 | Thangaraj et al. | |
| 6,277,363 B1 | 8/2001 | Ratcliff | |
| 6,306,281 B1 * | 10/2001 | Kelley | ............... 205/556 |
| 6,432,322 B1 | 8/2002 | Speronello et al. | |
| 2004/0166136 A1 | 8/2004 | Morelli et al. | |
| 2006/0068029 A1 | 3/2006 | Mason | |
| 2010/0028456 A1 | 2/2010 | Fukuda et al. | |

FOREIGN PATENT DOCUMENTS

| | | |
|---|---|---|
| EP | 2130542 A1 | 12/2009 |
| JP | 36-8135 B1 | 6/1961 |
| JP | 49-111898 A | 10/1974 |
| JP | 61-19561 B2 | 5/1986 |
| JP | 61-181532 A | 8/1986 |
| JP | 63-309599 A | 12/1988 |
| JP | 1-319408 A | 12/1989 |
| JP | 4-46003 A | 2/1992 |
| JP | 11-278808 A | 10/1999 |
| JP | 3110724 B2 | 9/2000 |
| JP | 2007-217239 A | 8/2007 |
| WO | WO 95/02965 A1 | 2/1995 |
| WO | WO 2004/032979 A2 | 4/2004 |
| WO | WO 2005/115416 A2 | 12/2005 |

OTHER PUBLICATIONS

International Search Report dated May 1, 2008 in corresponding International Application No. PCT/JP2008/052496.
Kagaku Binran Kisohen, Sep. 25, 1966, p. 1054, Maruzen Co., Ltd. (International Search Report).
Extended European Search Report issued in corresponding European Application No. EP 08 71 1326 on Nov. 21, 2012.

* cited by examiner

*Primary Examiner* — Peter F Godenschwager
(74) *Attorney, Agent, or Firm* — Buchanan Ingersoll & Rooney PC

(57) ABSTRACT

A composition for stabilizing chlorine dioxide maintains a chlorine dioxide concentration nearly constant in the agent containing chlorine dioxide dissolved therein even when chlorine dioxide is continuously released as gas from agent, and includes a chlorite and a pH adjuster. The pH adjuster is an acid or a salt thereof having a buffering property whose pH is 2.5 to 6.8 as a 5% aqueous solution at 25° C.

5 Claims, 1 Drawing Sheet

COMPOSITION FOR STABILIZING CHLORINE DIOXIDE

CROSS REFERENCE TO RELATED APPLICATIONS

This application is a divisional of application Ser. No. 12/531,254, filed Sep. 14, 2009, which was the National Stage filing under §371 of PCT/JP2008/052496, filed Feb. 15, 2008, which in turn claims priority to Japanese Application No. 2007-067179, filed Mar. 15, 2007, wherein the contents of each of the above applications are incorporated herein by reference.

TECHNICAL FIELD

The present invention relates to a composition for stabilizing chlorine dioxide (hereinbelow, frequently simply referred to as "stabilizing composition") which can maintain a chlorine dioxide concentration constant for a long term in an agent containing chlorine dioxide dissolved therein, that is, which can maintain the chlorine dioxide concentration nearly constant even when chlorine dioxide is continuously released by portions as gas from the agent (or even when chlorine dioxide gas is aggressively kept released).

BACKGROUND ART

It is well known that chlorine dioxide gas is a strong oxidant, and its oxidizing action is effective in sterilization and decomposition of malodorous substances. Therefore, chlorine dioxide has been used in disinfectant, deodorant and the like. Chlorine dioxide is dissolved in water in 20 times its volume of water, to give a brownish yellow aqueous solution. From the viewpoint of easiness in handling, it is desirable to use chlorine dioxide in a form of such an aqueous solution. However, when the aqueous solution of chlorine dioxide is brought into contact with air, chlorine dioxide gas is rapidly generated. Therefore, there has been proposed a technique in which chlorine dioxide gas is constantly generated while maintaining its stability, by dissolving chlorine dioxide gas in an aqueous solution of sodium peroxycarbonate, and thus by forming an aqueous solution containing sodium chlorite as a main component at a retained pH of 9, i.e., what is called a stabilized aqueous solution of chlorine dioxide (see Patent Document 1).

The stabilized aqueous solution of chlorine dioxide is retained at pH 9 (alkali) for the purpose of maintaining stability, as described above. Therefore, a generation amount of free chlorine dioxide gas having disinfecting and deodorizing effects or the like is extremely low, and thus it is difficult to attain satisfactory disinfecting and deodorizing effects or the like. Therefore, in order to enhance the activity of the stabilized aqueous solution of chlorine dioxide, an acid has been added immediately before its use to lower the pH to 7 or less, for generating chlorine dioxide gas, to thereby elicit activity.

However, the generation of chlorine dioxide gas is extremely rapid, and chlorine dioxide does not have sustained activity. As a result, there arise economical problems that processes and equipments or facilities to implement the processes are required in order to activate the chlorine dioxide solution and to continuously generate chlorine dioxide gas. In addition, since chlorine dioxide gas is rapidly generated in the conventional stabilized aqueous solution of chlorine dioxide as described above, a chlorine dioxide activity is not retained constant and sometimes reaches an extremely high level, which raises safety concern about effects on animals, especially on human being, and the chlorine dioxide has not been used without anxiety.

In order to solve the above-mentioned problems, there has been proposed a technique in which a mixture prepared by adding an organic acid, such as citric acid, to chlorite is blended with a dissolved chlorine dioxide solution, to thereby maintain a chlorine dioxide concentration nearly constant for a long term (see Patent Document 2).

Patent Document 1: Japanese Patent Application JP61-181532A
Patent Document 2: Japanese Patent JP3110724B

SUMMARY

According to the technique disclosed in Patent Document 2, the chlorine dioxide concentration can be maintained constant for a long term without rapidly generating gas, and even when chlorine dioxide is continuously released by portions as gas, the chlorine dioxide concentration can be held in an approximately constant range. However, the preservation stability is not necessarily satisfactory, and there is a room for improvement.

The present invention is made with the view toward solving the above-mentioned problems, and the object is to provide a stabilizing composition having excellent preservation stability, in which the chlorine dioxide concentration of the agent containing chlorine dioxide can be held in an approximately constant range for a long term.

In one aspect of the present invention, a composition for stabilizing chlorine dioxide, which can maintain a chlorine dioxide concentration nearly constant in an agent containing chlorine dioxide dissolved therein even when chlorine dioxide is continuously released as gas from the agent, includes a chlorite and a pH adjuster which is an acid or a salt thereof having a buffering property whose pH is 2.5 to 6.8 as a 5% aqueous solution at 25° C.

According to the stabilizing composition of the present invention, excellent preservation stability can be obtained. For example, the chlorine dioxide concentration of the agent containing chlorine dioxide can be maintained constant for a long term, and even when chlorine dioxide is continuously released by portions as gas from the agent (or even when chlorine dioxide gas is aggressively kept released), the chlorine dioxide concentration in the agent can be held in an approximately constant range. The expression "continuously released by portions as gas" herein means that, for example, during transportation or preservation, even though a lid of a container is closed, chlorine dioxide dissipates as gas in the course of nature, and the expression "chlorine dioxide gas is aggressively kept released" herein means that chlorine dioxide gas is released to a gas phase with an expectation of obtaining deodorizing and disinfecting action in the gas phase.

Herein, it is preferable that the pH adjuster is phosphoric acid or a salt thereof.

When phosphoric acid or a salt thereof is used as the pH adjuster, as compared with other inorganic acids or organic acids, preservation stability is further improved (period with preservation stability is further extended), and a change in a liquid property (pH) over time during preservation is suppressed.

In addition, it is preferable that the pH adjuster is sodium dihydrogenphosphate or a mixture of sodium dihydrogenphosphate with disodium hydrogenphosphate.

Moreover, by selecting sodium dihydrogenphosphate or the mixture of sodium dihydrogenphosphate with disodium hydrogenphosphate, and by combining this with sodium chlorite, an excessive progression of a reaction in which sodium chlorite turns into chlorine dioxide hardly occurs. Therefore, a gas equilibration state is retained by replenishing chlorite ion from sodium chlorite that compensates only chlorine dioxide that is lost by natural decomposition or that dissipates from a lid portion or walls of the container. As described above, the present invention is suitable in that unnecessary consumption of sodium chlorite is suppressed and sodium chlorite is efficiently consumed, leading to further improvement in preservation stability (period with preservation stability is further extended), and to further suppression of a change in chlorine dioxide concentration over time during preservation (both the decrease and increase in the concentration can be suppressed). In addition, a mechanism of the chlorine dioxide solution containing the stabilizing composition of the present invention for replenishing chlorine dioxide from sodium chlorite for a long term is exerted even in a space or on a subject, to which the solution is applied, sprayed or diffused. This provides an excellent sustained effect, i.e. lasting disinfecting and deodorizing activity after application, spraying or diffusion of the solution, further providing a great merit to the user upon its use.

DETAILED DESCRIPTION

Figure 1:
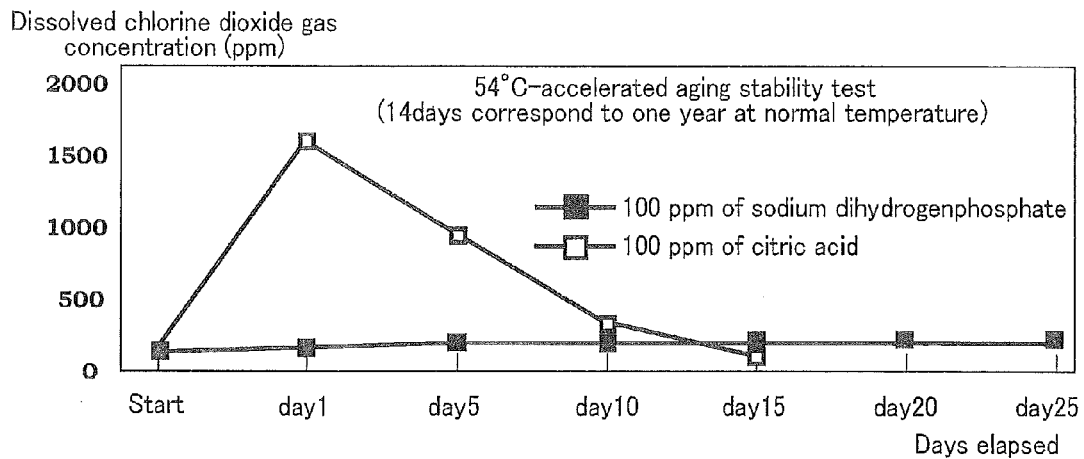
FIG. 1 is a graph showing dissolved chlorine dioxide gas concentration in a case where sodium dihydrogenphosphate was used in an amount of a reaction equivalent or more and a case where citric acid was used in an amount of a reaction equivalent or more (the initial concentration was 100 ppm)
Figure 2:
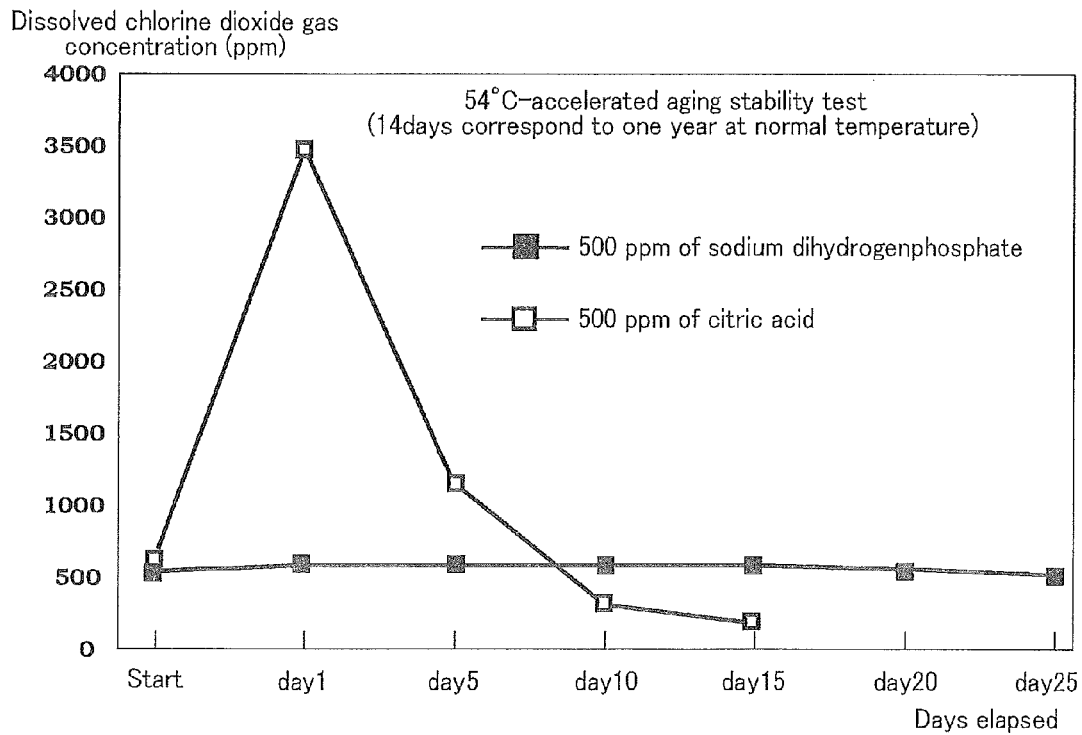
FIG. 2 is a graph showing dissolved chlorine dioxide gas concentration in a case where sodium dihydrogenphosphate was used in an amount of a reaction equivalent or more and a case where citric acid was used in an amount of a reaction equivalent or more (the initial concentration was 500 ppm).

An embodiment of the present invention will be described below, but the present invention should not be limited to this embodiment.

(Chlorite)

For the chlorite to be used in the present invention, for example, salts of alkali metal chlorite and salts of alkali earth metal chlorite can be mentioned. Examples of the salt of alkali metal chlorite include sodium chlorite, potassium chlorite and lithium chlorite. Examples of the salt of alkali earth metal chlorite include calcium chlorite, magnesium chlorite and barium chlorite. Especially, not only from the viewpoint of availability, but also from the viewpoint of long-term preservation stability of the dissolved chlorine dioxide gas, sodium chlorite and potassium chlorite are preferable, and sodium chlorite is most preferable.

(pH Adjuster)

For the pH adjuster to be used in the present invention, an acid (inorganic acid and organic acid) or a salt thereof, having a buffering property whose pH is 2.5 to 6.8 as a 5% aqueous solution at 25° C., can be mentioned. When the pH is below 2.5, or above 6.8, the preservation stability of the dissolved chlorine dioxide is reduced, and a change in a liquid property (pH) of the chlorine dioxide solution during preservation becomes large. It is preferable to use an acid (inorganic acid and organic acid) or a salt thereof having a buffering property whose pH is 3.5 to 6.0 as a 5% aqueous solution at 25° C., and it is more preferable to use one having a pH of 4.0 to 5.5. Examples of the acid include phosphoric acid, boric acid, metaphosphoric acid, pyrophosphoric acid, sulfamic acid and acetic acid, and from the viewpoint of obtaining excellent preservation stability, inorganic acid or a salt thereof is preferred. Examples of the salt thereof include sodium dihydrogenphosphate and a mixture of sodium dihydrogenphosphate with disodium hydrogenphosphate. Especially, phosphoric acid or a salt thereof is preferred, and sodium dihydrogenphosphate is more preferred, since preservation stability is excellent and a change in the liquid property (pH) during preservation is suppressed to a minimum, leading to excellent disinfecting action, antiviral action, antifungal action, deodorizing action or the like. It should be noted that one kind of the pH adjuster may be used alone or two or more kinds thereof may be used in combination. The final pure chlorine dioxide solution has a pH of preferably 4.5 to 6.5, more preferably 5.5 to 6.0, since preservation stability is excellent for a long term, and a pH change during preservation is suppressed.

(Preparative Example of Stabilizing Composition)

The stabilizing composition of the present invention including the chlorite and the pH adjuster (an acid or a salt thereof having a buffering property whose pH is 2.5 to 6.8 as a 5% aqueous solution at 25° C.) may be, for example, obtained in the following manner. Specifically, a chlorite is dissolved in water to prepare 2,000 to 180,000 ppm of an aqueous chlorite solution, and in the solution is dissolved a pH adjuster to prepare a stabilized solution. The amount of the pH adjuster is, for example, 0.5 to 100 g per 1,000 ml of the aqueous chlorite solution, with which the pH of the dissolved chlorine dioxide solution becomes 4.5 to 6.5, preferably 5.5 to 6.0.

(Preparative Example of Chlorine Dioxide Solution)

The chlorine dioxide solution may be, for example, obtained in the following manner. Specifically, (a) a chlorite is dissolved in water to prepare 2,000 to 180,000 ppm of an aqueous solution of sodium chlorite, and (b) chlorine dioxide gas is bubbled and dissolved in water to prepare 100 to 2,900 ppm of an aqueous solution of chlorine dioxide.

Subsequently, 5.0 to 990 ml, preferably 50 to 300 ml of the aqueous solution of chlorous acid (item (a)), 5.0 to 990 ml, preferably 50 to 800 ml of the aqueous solution of chlorine dioxide (item (b)) and 5.0 to 990 ml, preferably 50 to 400 ml of the stabilizing composition are mixed and stirred well at room temperature to thereby prepare a chlorine dioxide solution.

It is preferred that the final pH of the pure chlorine dioxide solution is 4.5 to 6.5. When the pH is out of this range, the preservation stability is reduced, which may lead to, for example, fluctuation of the pharmacological activity during preservation, and to attenuation in the pharmacological activity after long-term (e.g. 2-year) preservation. In the present invention, more preferable pH range of the pure chlorine dioxide solution is 5.5 to 6.0.

Example 1

In the following manner, a chlorine dioxide solution was prepared. Specifically, to 250 ml of water in which 2,000 ppm of chlorine dioxide gas had been dissolved were added 680 ml of water and then 80 ml of a 25% solution of sodium chlorite, and stirred. Subsequently, to the solution was added sodium dihydrogenphosphate (having a pH of 4.1 to 4.5 as a 5% aqueous solution at 25° C.) in such an amount that the pH of the solution became 5.5 to 6.0 and stirred, to thereby obtain 1,000 ml of a chlorine dioxide solution including: a chlorine dioxide gas dissolved therein; and a stabilizing composition including sodium chlorite and sodium dihydrogenphosphate.

Comparative Example 1

A chlorine dioxide solution as a control was prepared in the same manner as in Example 1, except that citric acid (having a pH of 1.8 to 2.2 as a 5% aqueous solution at 25° C.) was used instead of sodium dihydrogenphosphate.

(Stabilizing Test)

The chlorine dioxide solution obtained in Example 1 was diluted by a conventional method, to thereby prepare chlorine dioxide solutions having concentrations of 100 ppm and 500 ppm. Likewise, the chlorine dioxide solution obtained in Comparative Example 1 was used to thereby prepare solutions having chlorine dioxide concentrations of 100 ppm and 500 ppm.

In order to determine the preservation stability of these solutions, changes in the chlorine dioxide concentration (ppm) and in the liquid property (pH) over time were measured. For the stabilizing test, an accelerated aging test (measurement temperature: 54° C., 14 days correspond to one year at normal temperature) was performed in accordance with a conventional method. The results of the preservation stability are shown in Tables below and the drawings (comparative data is shown between a case where sodium dihydrogenphosphate was used in an amount of a reaction equivalent or more and a case where citric acid was used in an amount of a reaction equivalent or more).

TABLE 1

| *54° C.-accelerated aging test (14 days correspond to one year at normal temperature) | | | |
|---|---|---|---|
| (Concentration: 100 ppm, sodium dihydrogenphosphate was used) | | (Concentration: 100 ppm, citric acid was used) | |
| | Dissolved ClO$_2$ (ppm) | | Dissolved ClO$_2$ (ppm) |
| Start | 116 | Start | 121 |
| 1 day later | 143 | 1 day later | 1,551 |
| 5 days later | 154 | 5 days later | 935 |
| 10 days later | 149 | 10 days later | 269 |
| 15 days later | 128 | 15 days later | 69 |
| 20 days later | 128 | 20 days later | — |
| 25 days later | 129 | 25 days later | — |

TABLE 2

| *54° C.-accelerated aging test (14 days correspond to one year at normal temperature) | | | |
|---|---|---|---|
| (Concentration: 500 ppm, sodium dihydrogenphosphate was used) | | (Concentration: 500 ppm, citric acid was used) | |
| | Dissolved ClO$_2$ (ppm) | | Dissolved ClO$_2$ (ppm) |
| Start | 523 | Start | 567 |
| 1 day later | 554 | 1 day later | 3,474 |
| 5 days later | 546 | 5 days later | 1,160 |
| 10 days later | 532 | 10 days later | 286 |
| 15 days later | 538 | 15 days later | 150 |
| 20 days later | 516 | 20 days later | — |
| 25 days later | 476 | 25 days later | — |

As is apparent from the above-described tables and accompanied drawings, the pH adjuster whose pH is 2.5 to 6.8 as a 5% aqueous solution at 25° C. remarkably enhances the preservation stability of the chlorine dioxide solution, and suppresses a change in the liquid property (pH) during preservation, as compared with an acid having a buffering property whose pH is outside the range of from 2.5 to 6.8. Accordingly, for example, when dissolved chlorine dioxide is used in disinfectant, deodorant, antifungal agent or the like, the stabilizing composition of the present invention can provide highly reliable products to the market.

INDUSTRIAL APPLICABILITY

The stabilizing composition according to the present invention is suitably utilized in an agent containing chlorine dioxide, such as disinfectant, deodorant and fungicide, in order to hold the chlorine dioxide concentration in an approximately constant range for a long term.

The invention claimed is:

1. A method for preparing a chlorine dioxide solution, the method comprising:
   [1] separately preparing each of a solution (A) and a solution (B), wherein solution (A) is a solution in which a chlorine dioxide gas is dissolved, and solution (B) is a solution comprising a chlorite;
   [2] mixing the solution (A) and the solution (B); and
   [3] adding phosphoric acid or a salt thereof as a pH adjuster to the solution mixture resulting from step [2].

2. The method of claim 1, wherein step [3] includes adding phosphoric acid or a salt thereof as the pH adjuster to the solution mixture resulting from step [2] to adjust the pH to 4.5 to 6.5.

3. The method of claim 1, wherein step [3] includes adding phosphoric acid or a salt thereof as the pH adjuster to the solution mixture resulting from step [2] to adjust the pH to 5.5 to 6.0.

4. The method of claim 1, wherein the pH adjuster is selected from the group consisting of sodium dihydrogenphosphate and a mixture of sodium dihydrogenphosphate with disodium hydrogenphosphate.

5. The method of claim 1, wherein the chlorite is sodium chlorite.

* * * * *